(12) United States Patent
Hellstrom et al.

(10) Patent No.: US 10,786,205 B2
(45) Date of Patent: *Sep. 29, 2020

(54) SENSING CATHETER EMITTING RADIANT ENERGY

(71) Applicants: Ake A. Hellstrom, Columbus, OH (US); Errol O. Singh, Columbus, OH (US)

(72) Inventors: Ake A. Hellstrom, Columbus, OH (US); Errol O. Singh, Columbus, OH (US)

(*) Notice: Subject to any disclaimer, the term of this patent is extended or adjusted under 35 U.S.C. 154(b) by 1016 days.

This patent is subject to a terminal disclaimer.

(21) Appl. No.: 14/473,812

(22) Filed: Aug. 29, 2014

(65) Prior Publication Data

US 2016/0058383 A1    Mar. 3, 2016

Related U.S. Application Data

(63) Continuation of application No. 14/124,435, filed as application No. PCT/US2012/040877 on Jun. 5, 2012.

(51) Int. Cl.
| | |
|---|---|
| *A61B 5/00* | (2006.01) |
| *A61B 1/07* | (2006.01) |
| *A61B 1/06* | (2006.01) |
| *A61B 1/015* | (2006.01) |
| *A61B 1/307* | (2006.01) |
| *G02B 23/24* | (2006.01) |
| *A61B 1/05* | (2006.01) |

(Continued)

(52) U.S. Cl.
CPC ............ *A61B 5/6852* (2013.01); *A61B 1/015* (2013.01); *A61B 1/05* (2013.01); *A61B 1/0607* (2013.01); *A61B 1/0676* (2013.01); *A61B 1/0684* (2013.01); *A61B 1/07* (2013.01); *A61B 1/307* (2013.01); *G02B 23/2461* (2013.01); *G02B 23/2484* (2013.01); *A61B 5/0071* (2013.01); *A61B 5/0075* (2013.01); *A61B 5/0086* (2013.01); *A61B 5/015* (2013.01); *A61B 5/0507* (2013.01); *A61B 6/4057* (2013.01)

(58) Field of Classification Search
CPC ....................... G02B 23/2461; G02B 23/2484; A61B 1/015; A61B 1/05; A61B 1/0607; A61B 1/0676; A61B 1/0684; A61B 1/07; A61B 1/307; A61B 5/6852; A61B 5/0071; A61B 5/0075; A61B 5/0086; A61B 5/015; A61B 5/0507; A61B 6/4057
See application file for complete search history.

(56) References Cited

U.S. PATENT DOCUMENTS

| | | | |
|---|---|---|---|
| 3,902,880 A | 9/1975 | Strack | |
| 4,418,688 A * | 12/1983 | Loeb | ................. A61B 1/00082 600/106 |

(Continued)

FOREIGN PATENT DOCUMENTS

| | | |
|---|---|---|
| JP | 2004-29235 A | 1/2004 |
| JP | 2010-57960 A | 3/2010 |

(Continued)

*Primary Examiner* — Theodore J Stigell
*Assistant Examiner* — Sean A Frith

(57) ABSTRACT

Provided is a sensing catheter having an outer flexible sheath and a proximal section containing a sensing system having a sensing means, a radiant energy providing means and radiation transmitting means, preferably all housed within a fluid channel.

50 Claims, 20 Drawing Sheets

(51) Int. Cl.
*A61B 5/05* (2006.01)
*A61B 6/00* (2006.01)
*A61B 5/01* (2006.01)

(56) References Cited

U.S. PATENT DOCUMENTS

| | | | |
|---|---|---|---|
| 5,237,984 A | 8/1993 | Williams, III et al. | |
| 5,363,838 A | 11/1994 | George | |
| 5,608,834 A | 3/1997 | Van Leeuwen | |
| 5,833,683 A * | 11/1998 | Fuller | A61B 18/22 606/17 |
| 6,190,380 B1 * | 2/2001 | Abela | A61B 18/24 606/28 |
| 7,030,904 B2 | 4/2006 | Adair et al. | |
| 7,442,167 B2 | 10/2008 | Dunki-Jacobs et al. | |
| 7,922,650 B2 | 4/2011 | McWeeney et al. | |
| 7,922,654 B2 | 4/2011 | Boutillette et al. | |
| 2002/0087047 A1 | 7/2002 | Remijan et al. | |
| 2003/0120271 A1 | 6/2003 | Burnside et al. | |
| 2004/0006333 A1 | 1/2004 | Arnold et al. | |
| 2004/0097788 A1 * | 5/2004 | Mourlas | A61B 1/00082 600/116 |
| 2004/0111012 A1 | 6/2004 | Whitman | |
| 2005/0113685 A1 | 5/2005 | Maschke et al. | |
| 2005/0187422 A1 | 8/2005 | Maschke | |
| 2005/0187571 A1 | 8/2005 | Maschke | |
| 2005/0277808 A1 | 12/2005 | Sonnensche | |
| 2005/0283048 A1 | 12/2005 | Gill et al. | |
| 2005/0288546 A1 | 12/2005 | Sonnenschein et al. | |
| 2006/0025650 A1 | 2/2006 | Gavriely | |
| 2007/0027520 A1 * | 2/2007 | Sherburne | A61F 2/958 623/1.11 |
| 2007/0161853 A1 | 7/2007 | Yagi et al. | |
| 2007/0182842 A1 | 8/2007 | Sonnenschein et al. | |
| 2008/0015565 A1 | 1/2008 | Davison | |
| 2008/0082045 A1 * | 4/2008 | Goldfarb | A61B 1/00126 604/96.01 |
| 2008/0091064 A1 | 4/2008 | Laser | |
| 2008/0177138 A1 * | 7/2008 | Courtney | A61B 5/742 600/109 |
| 2009/0012367 A1 | 1/2009 | Chin et al. | |
| 2009/0054803 A1 * | 2/2009 | Saadat | A61B 17/3415 600/546 |
| 2009/0112198 A1 | 4/2009 | Khanna et al. | |
| 2009/0254074 A1 | 10/2009 | Splinter et al. | |
| 2009/0299363 A1 | 12/2009 | Saadat et al. | |
| 2009/0318757 A1 | 12/2009 | Singh | |
| 2009/0318798 A1 | 12/2009 | Singh et al. | |
| 2010/0016842 A1 | 1/2010 | Fix | |
| 2010/0030057 A1 | 2/2010 | Gavriely et al. | |
| 2010/0069713 A1 | 3/2010 | Endo et al. | |
| 2010/0198012 A1 | 8/2010 | Poole et al. | |
| 2010/0204546 A1 | 8/2010 | Hassidov et al. | |
| 2010/0217080 A1 | 8/2010 | Cheung et al. | |
| 2010/0238279 A1 | 9/2010 | Thoms et al. | |
| 2010/0245549 A1 | 9/2010 | Allen et al. | |
| 2010/0286475 A1 | 11/2010 | Robertson | |
| 2011/0028790 A1 | 2/2011 | Farr et al. | |
| 2011/0118547 A1 | 5/2011 | Erikawa | |
| 2011/0288372 A1 | 11/2011 | Petersen | |

FOREIGN PATENT DOCUMENTS

| | | |
|---|---|---|
| WO | 2004/026125 A1 | 4/2004 |
| WO | 2010/146587 A1 | 12/2010 |

* cited by examiner

SENSING CATHETER EMITTING RADIANT ENERGY

This application is a continuation application of U.S. application Ser. No. 14/124,435, filed on Dec. 6, 2013, as a national stage entry of PCT/US2012/040877, filed on Jun. 5, 2012, which claims benefit of U.S. Provisional Application 61/493,521, filed Jun. 6, 2011.

BACKGROUND OF THE INVENTION

This invention is in the technical field of medical instruments, in particular for sensing, especially vision equipped, catheters, for insertion in narrow body lumens or passages. As an example, urinary catheters with vision and/or other sensing devices have to fit within the very narrow confines and thin fragile walls of the urethra.

In a first consideration, this requirement drives such instruments to have a very small cross section and a well tapered entry portion at the tip to allow safe insertion with minimum patient discomfort or risk for procedure complications.

But in a second consideration, there are also major benefits to include multiple functionalities in the instrument to be inserted in the body. This may consist of a subset, or all of, multiple fluid passages, vision systems, illumination devices, mechanical instruments and energy emission devices for diagnostics, absorption or treatment. To fit this into the confines of a small diameter instrument with tapered entry section poses a major challenge. This has made it difficult to combine desired functionality. As one example, there are recent commercial developments in subminiature cameras for vision in the tip of endoscopes. However, the very restricted dimensions that are permissible in for instance urinary catheters, make it very challenging to fit even a state of the art subminiature camera and required additional functionality in the instrument tip.

Imaging fiber optic bundles have been applied for remote vision devices a distance away from the instrument tip. These have the disadvantage of high cost due to the precision sorted arrangement of fibers in both ends. They have also the particular disadvantage of poor image resolution in small diameter applications due to the limited number of fibers that can be fitted in a small cross section. This limits the image clarity for the operator and may result in more difficult decisions due to lack of small details in the image.

A particular requirement for some vision equipped catheters, for instance in urology, is that often catheters must stay in place for an extended time after insertion, for fluid drainage or other liquid handling purposes. This poses a challenge to conventional inserted advanced instruments that may include tip mounted cameras, illumination, sensors, actuators or other devices. There is a need to disconnect such devices for long term catherization since they may also impede the liquid flow if staying in place and also create patient discomfort. It would be an advantage if all such extra functions can be easily removed while catheter is in place and leave only fluid channels.

As instruments like catheters advance in the art of added functionality and features, there is a need to keep the cost down. This can be achieved by a system design that allows flexibility of providing added features only as needed for a particular situation. It would for instance be an advantage if there is a simple catheter sleeve utilized for all applications, plus an insert that can be tailored for the need of a particular procedure.

When electric devices like cameras, illumination, sensors, actuators and treatment energy sources are introduced in the inserted portion of catheters or endoscopes, there is also a need to connect them to the outside world. Various schemes have been suggested including wires embedded in catheter walls, miniature connectors in the catheter tip, or wireless transmission equipment in the catheter tip for power and/or data. All such methods are feasible in large diameter endoscopic applications but become more challenging for very small diameter applications, like urinary catheters with fluid handling and vision. The available space for payload inside such a catheter is just too small to economically include too many electric devices while creating reliable mating electric connections in liquid environment. Insulated electric cables permanently attached and sealed to devices inside the catheter and tip is one viable solution. It is also desired to keep the count of wires low to reduce electric wiring cross section area and improve reliability.

SUMMARY OF THE INVENTION

The present invention alleviates the current problems in packaging additional functionality in small diameter, tapered tip catheters and other similar medical instruments. It does this by a design that permits shared simultaneous use of a common shared cross sectional area in the catheter tip by multiple functions. For instance, irrigation or other clear liquid or gas passages or orifices may also have a second role as illumination guides for a patient observation device, or as energy guide for devices directing radiant treatment energy towards the patient.

In another aspect of the invention, the restricted cross section problem is solved by locating the energy source or sources behind the observation device in the length direction from the distal end catheter tip. The energy source location behind the observation device allows larger footprint illumination or treatment devices with more emitted power and model versatility. The radiated energy is then carried around the observation device by means of a reflective surface on the inside of the instrument hollow distal tip and optionally on the observation device housing, creating an annular light guide for illumination. The tip may optionally be made of a translucent material to deliver a combination illumination of the target of both reflected and transmitted light. This light guide may also simultaneously share the role as a liquid or gas channel, for instance for irrigation. The observation device may be a camera or other imaging device, or other radiant energy sensors like for radiant temperature, thermal imaging, reflected energy spectral analyzer, color, texture or fluorescence analysis. The illumination or treatment devices or sources may be one or more LED's, lasers, or other radiant energy sources utilized for patient observation, diagnostics or treatment. The type of radiant energy involved includes visible light, UV, infrared, microwave, RF, THz or X-ray or a combination thereof. The radiant energy may be one single type, or simultaneous multiple types, or alternated between energy types selected to provide desired medical results. This includes for instance forward vision for observing safe instrument insertion, visualization of internal surgical procedures, patient diagnostics, antimicrobial treatment, photo activation of drugs, and internal tissue phototherapy for healing.

In yet another aspect of the invention, the illumination or treatment source is remoted from the instrument tip and utilizes of one or more fiber optics bundles or optical fibers leading to a light exit fiber end behind the sensor and using reflective surfaces on the inside of the tip and optionally on the sensor housing, guiding light or other energy for illumination or treatment in the annular channel of the instrument tip, where this light guide may also serve as a liquid channel.

In yet another aspect of the invention, the imaging can also be achieved via an imaging fiber optics bundle as a sensor at the tip and locating a camera at the other end of the fiber bundle remoted from the patient.

In one different aspect of the invention, the catheter for insertion into a patient lumen consists of a passive outer sleeve and an instrumented inner assembly that is insertable and removable in the sleeve from the proximal end of the sleeve away from the patient. This inner assembly will accommodate functions that are not part of the outer sleeve, including camera, illumination and treatment devices, sensors, or it may alternatively house fiber optics for remote imaging and illumination, actuators or treatment sources.

In one additional aspect of the invention, the inner member may include one or more lumen for liquid, for instance for irrigation.

In another aspect of the invention, the inner member may contain instruments for vision, illumination, treatment devices, actuators, and also electric conductors, for instance camera and light source wires.

In yet another aspect of the invention, the inner member houses no additional devices but may act as just an additional fluid channel or a stiffener.

In yet another aspect of the invention, the inner member provides additional stiffness to the sleeve for insertion or withdrawal control.

In yet another aspect of the invention, the stiffness of the the sleeve varies according to the length position of the instrument to match the anatomy profile of the patient and avoid collapse.

In yet another aspect of the invention, the sleeve may be constructed of a thin wall and light flexible material for improved patient comfort, while the removable inner member provides stiffness for insertion.

In yet another aspect of the invention, the inner member is positionable in the length direction of the sleeve, and removable while the sleeve remains inserted in the patient.

Thus, in accordance with the present invention, there is provided a sensing catheter for use in a narrow body lumen having a distal catheter section terminating in an inwardly tapered port and containing a sensing system comprising (1) a sensing means having a sensor for sensing a radiant energy from the lumen as the catheter travels through or stops within the lumen, (2) radiant energy providing means located in the distal catheter section behind the sensor and (3) radiation transmitting means for transmitting radiant energy emitted by the radiant energy providing means around the sensing means and into the body lumen.

More particularly, in accordance with the present invention, the distal catheter section also functions as a fluid or gas channel in which the sensing system sits. The fluid or gas channel will extend back to a fluid inlet or outlet port located in the proximal catheter section outside the patient.

In preferred embodiments of the invention, the, sensing system is housed within a insertable and removable assembly which can be positioned within an outer catheter sleeve for use and then withdrawn, leaving a fluid channel.

In a more preferred embodiment of the invention, when the assembly housing the sensing system is in operable position within the catheter sleeve, a fluid channel is formed between outer parts of the assembly and the catheter sleeve while another fluid channel is present within the assembly, each fluid channel communicating with a separate port within the catheter distal section.

In one preferred embodiment of the invention, the radiant energy providing means is positioned behind and to the side of the front sensor of the sensing means, while in a more preferred embodiment, the radiant energy providing means is positioned behind and to the side of the entire sensing means.

BRIEF DESCRIPTION OF THE DRAWINGS

FIG. 1b shows a lengthwise perpendicular cross section of the tip of a catheter, as annotated in FIG. 1a.

DETAILED DESCRIPTION OF THE INVENTION

Figure 1A:
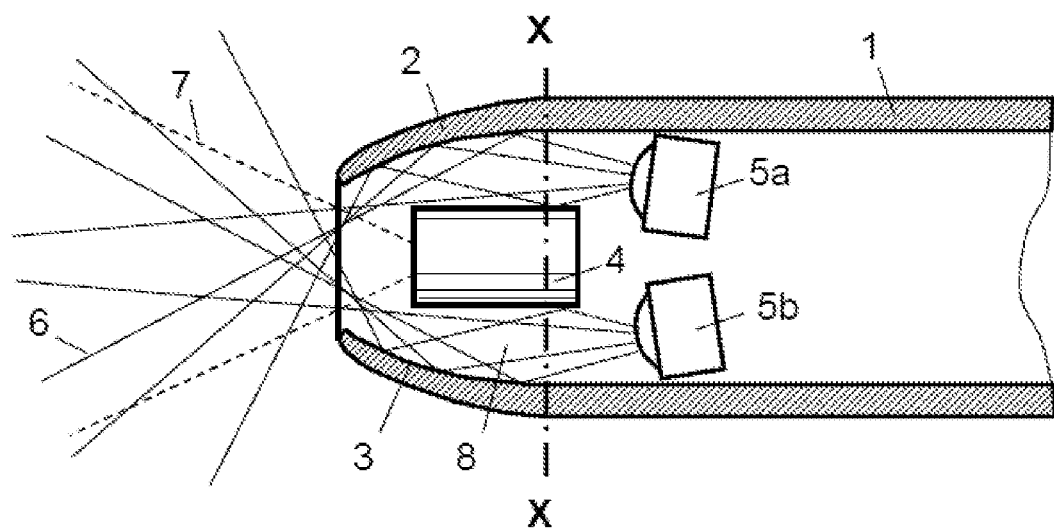
FIG. 1a shows a lengthwise cross section of the tip of a catheter, schematically illustrating the principle of illumination using reflected light from a light guide, two energy sources for illumination, and imaging using a camera.

This invention is best described by reference to each figure of the Drawing.

In FIG. 1a is illustrated the principle of the employment of the sensing system with a fluid channel. A catheter sleeve 1 has a tapered tip 2 for less traumatic and safer entry in patient lumen or narrow passages. On the interior side of the tip 2 is reflective surface 3 that directs the light or treatment radiation from one or more sources 5a, 5b into the patient, while passing around the camera 4 placed inside the tip 2. The sources 5a and 5b may be LEDs or lasers. By placing the sources behind the camera, space is gained for allowing larger components. The camera 4 may furthermore have a reflective exterior to improve illumination light guiding. The reflective surface 3 may have mirror finish or diffuse characteristics to achieve desired light patterns. The annular passage 8 between the camera 4 and the tip 2 may optionally also function as a fluid channel passing fluid or gas the same way as illumination light or other energy rays. This fluid can additionally serve as a means of keeping the camera lens area purged and clean. From an illumination standpoint, it is known that reflective surfaces act the same for interface to air or versus a liquid. The camera 4 may furthermore be slightly retracted behind the tip aperture for creating a clean fluid barrier for the vision. The light rays 6 emerging from the tip 2 illuminate the camera field of view 7 so the patient's interior can be observed.

Figure 1B:
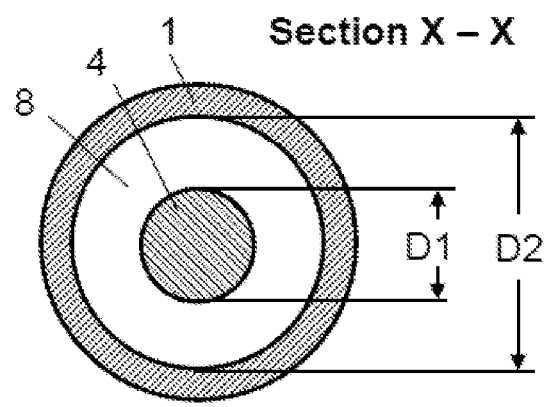

In FIG. 1b is schematically illustrated a perpendicular cross section of the tip 2 as designated by the line X-X located at a point of substantially maximum diameter of the catheter distal section in FIG. 1a. It is noted that the outside diameter of the camera D1 is less than the inside diameter of the catheter D2, forming annular channel 8 that may serve as both illumination path and fluid channel. The annular channel external diameter will contract close to the distal tip of the catheter. The diameter ratio D1/D2 may practically be in the range 0.2 to 0.8. Although everything here shown as circular cross sections, the shapes involved may also be rectangular, polygonal or elliptical.

In practice, the sensing catheter of the present invention will have a working outside maximum diameter of about 2 to 20 mm, preferably about 4 to 10 mm. Thus, the principles of the present invention can also be usefully employed in small diameter endoscopes requiring one or more fluid channels along with illumination or other provided radiant energy.

Figure 1C:
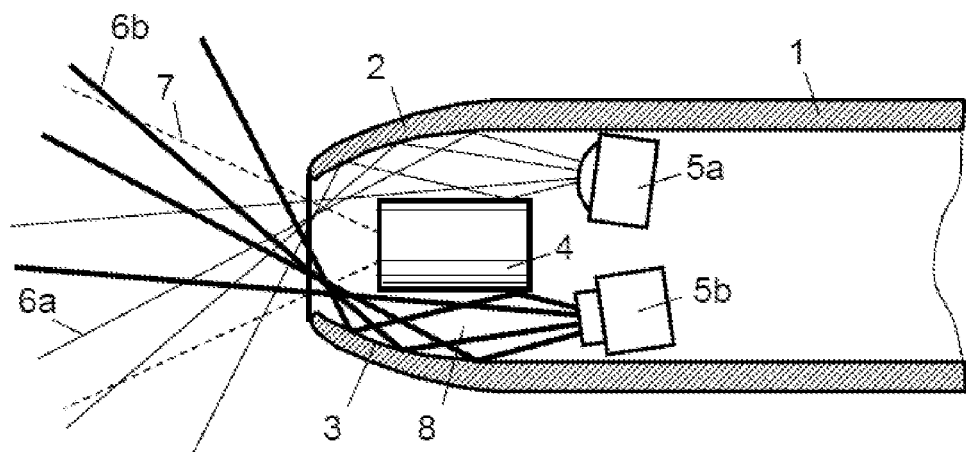
FIG. 1c shows a lengthwise cross section of the tip of a catheter, schematically illustrating the principle of illumination using reflected light from a light guide, and imaging using a camera, while using one energy source for illumination and one energy source for diagnostics or treatment.

In FIG. 1c is illustrated the configuration from FIG. 1a, but here with an illumination energy source 5a providing illumination rays 6a, and a different diagnostics or treatment energy source 5b providing diagnostics or treatment energy rays 6b which here are shown by darker lines for clarity. The energy sources 5a and 5b may be activated simultaneously or alternately and may be one or more of each type.

Figure 1D:
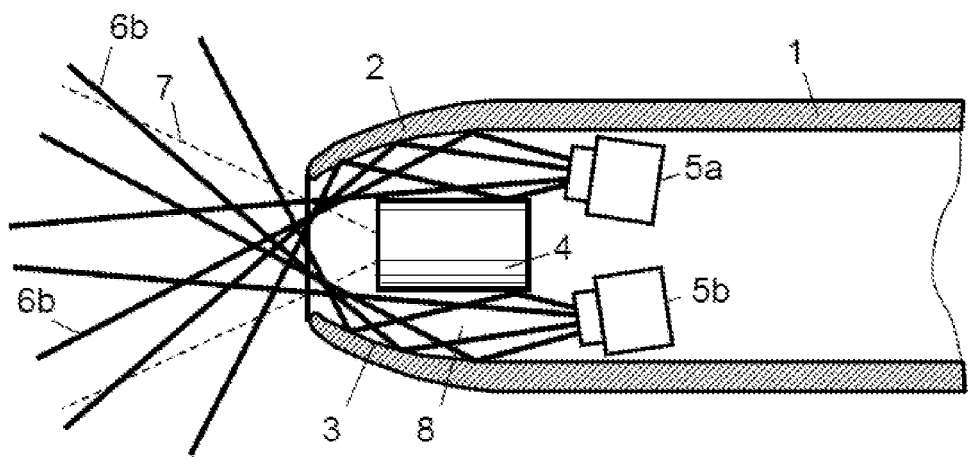
FIG. 1d shows a lengthwise cross section of the tip of a catheter, schematically illustrating the principle of with imaging using a camera, while using two energy sources for diagnostics or treatment.

In FIG. 1d is illustrated the configuration from FIG. 1a, but here with two diagnostics or treatment energy source 5a, and 5b providing diagnostics or treatment energy rays 6b which here are shown by darker lines for clarity. The energy sources 5a and 5b may be activated simultaneously or alternately, providing similar or different energy types, and may be one or more of each type.

Figure 2A:
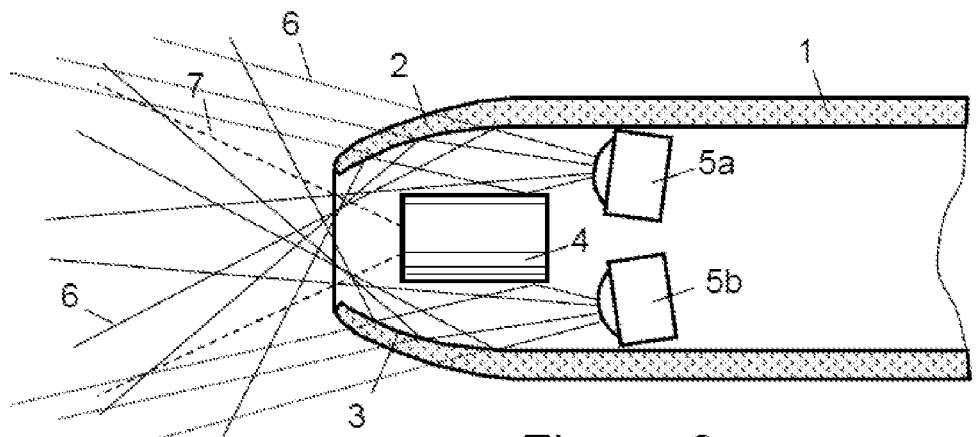
FIG. 2a shows a lengthwise cross section of the tip of a catheter, schematically illustrating the principle of illumination using both reflected light and transmitted light from a translucent and reflective light guide, two illumination sources, and imaging using a camera.

In FIG. 2a is illustrated the arrangement from FIG. 1, but here with the catheter tip 2 and reflective surface 3, made of a translucent or semi translucent material. Here, some light or other radiant energy rays 6 are reflected from the inside of the tip 2 similar to FIG. 1, but some rays 6 are also allowed to pass through the tip 2. This arrangement can be beneficial in creating different shape illumination patterns.

Figure 2B:
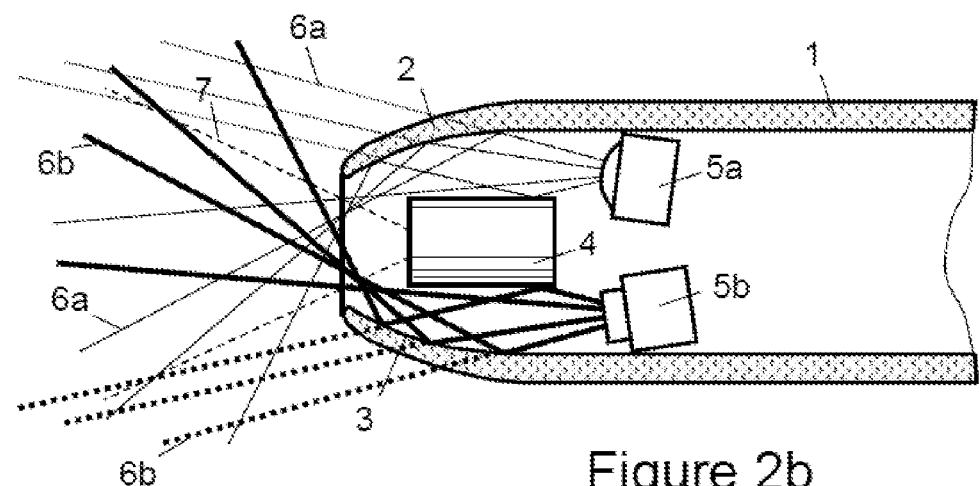
FIG. 2b shows a lengthwise cross section of the tip of a catheter, schematically illustrating the principle of illumination using both reflected and transmitted light from a light guide, and imaging using a camera, while using one energy source for illumination and one energy source for diagnostics or treatment.

In FIG. 2b is illustrated the arrangement from FIG. 2a but here with an illumination energy source 5a providing illumination rays 6a, and a different diagnostics or treatment energy source 5b providing diagnostics or treatment energy rays 6b which here are shown by darker lines for clarity. The energy sources 5a and 5b may be activated simultaneously or alternately and may be one or more of each type.

Figure 2C:
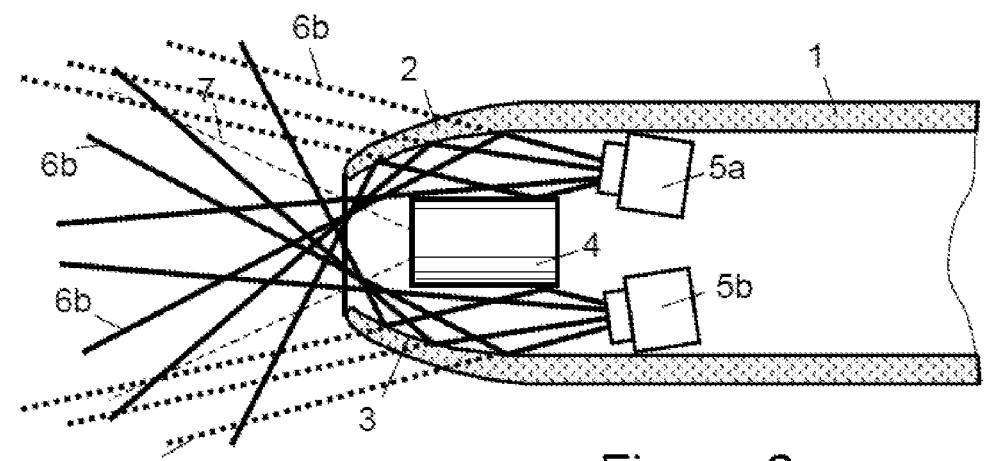
FIG. 2c shows a lengthwise cross section of the tip of a catheter, schematically illustrating the principle of illumination with imaging using a camera, while using two energy sources for diagnostics or treatment.

In FIG. 2c is illustrated the arrangement from FIG. 2a but here with two diagnostics or treatment energy source 5a, and 5b providing diagnostics or treatment energy rays 6b which here are shown by darker lines for clarity. The energy sources 5a and 5b may be activated simultaneously or alternately, providing similar or different energy types, and may be one or more of each type.

Figure 3:
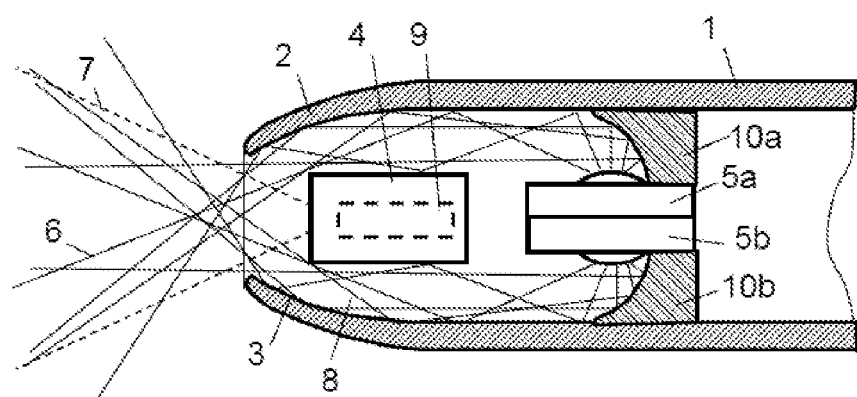
FIG. 3 shows a lengthwise cross section of the tip, schematically illustrating an alternate embodiment of illumination devices.

In FIG. 3 is shown a variation for one or more sources 5a and 5b, here mounted transversal to the camera 4 and illuminating via angled mirrors 10a and 10b. This allows sources with a wider foot print. The mirrors 10a and 10b can furthermore also serve to hold the sources 5a and 5b centered within the sleeve 1 or tip 2. The camera 9 may be centered in the tip via supports 9, which may be perpendicular to the mirrors 10a and 10b for minimum shading.

Figure 4:
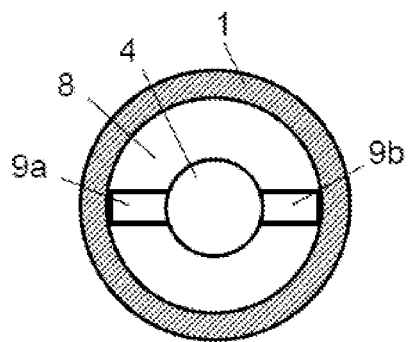
FIG. 4 shows a perpendicular cross section of the tip from FIG. 3, here taken at the location of the camera.

FIG. 4 shows a perpendicular cross section at the camera 4 of the configuration in FIG. 3. The camera is held in place or centered in the tip 2 of sleeve 1 by two or more supports 9a, 9b. The annular channel 8 provides illumination light guiding and optionally fluid flow.

Figure 5:
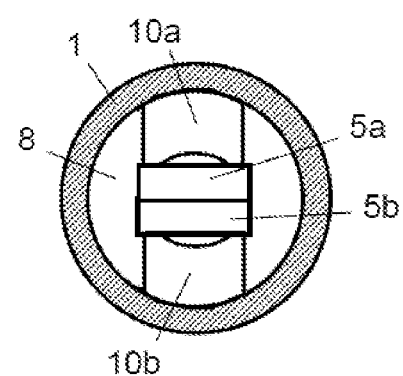
FIG. 5 shows a perpendicular cross section of the tip from FIG. 3, here taken at the location of the illumination.

FIG. 5 shows a perpendicular cross section at the sources 5a, 5b of the configuration in FIG. 4. The sources 5a, 5b may be held in place or centered in the tip 2 or sleeve 1 by the two mirrors 10a, 10b. The annular channel 8 provides flow on the side of the mirrors 10a, 10b.

Figure 6A:
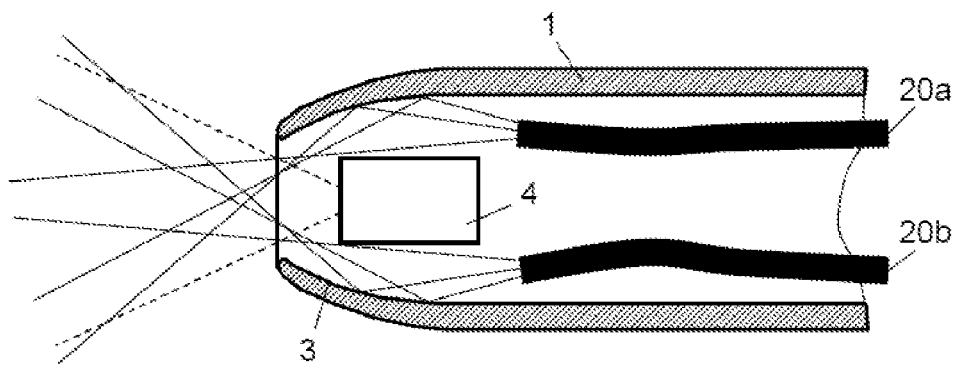
FIG. 6a shows a lengthwise cross section of the tip of a catheter, schematically illustrating an alternate embodiment of illumination using dual fiber optics and vision using a camera.

FIG. 6a shows yet another variation on the sensing catheter from FIG. 1, here using one or more fiber optics or other flexible energy guide assemblies 20a, 20b that send light or other radiant energy around the camera 4 because the radiant energy is guided by the reflective surface 3 inside the catheter tip, plus, to aid in energy conveyance, the exterior of camera 4 may also be reflective. The fiber optics assemblies receive light or treatment energy from remote sources arranged outside of the patient.

Figure 6B:
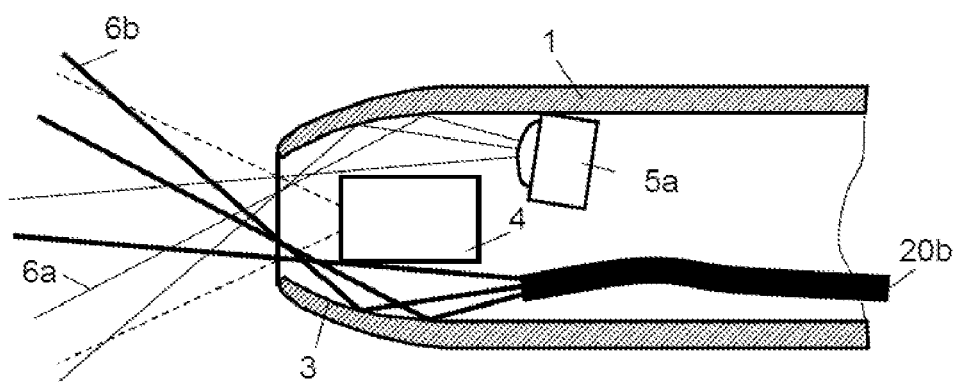
FIG. 6b shows a lengthwise cross section of the tip of a catheter, schematically illustrating an alternate embodiment of one illumination energy source behind the camera and one diagnostics or treatment energy source using fiber optics.

FIG. 6b shows yet another variation on the sensing catheter from FIG. 1a, here using one illumination energy source 5a behind the camera that directs rays 6a to the patient, and a fiber optics or other energy guiding assembly 20b that directs diagnostics or treatment radiant energy rays 6b which here are shown by darker lines for clarity. The fiber optics assembly receives diagnostics or treatment energy from remote sources arranged outside of the patient.

Figure 7:
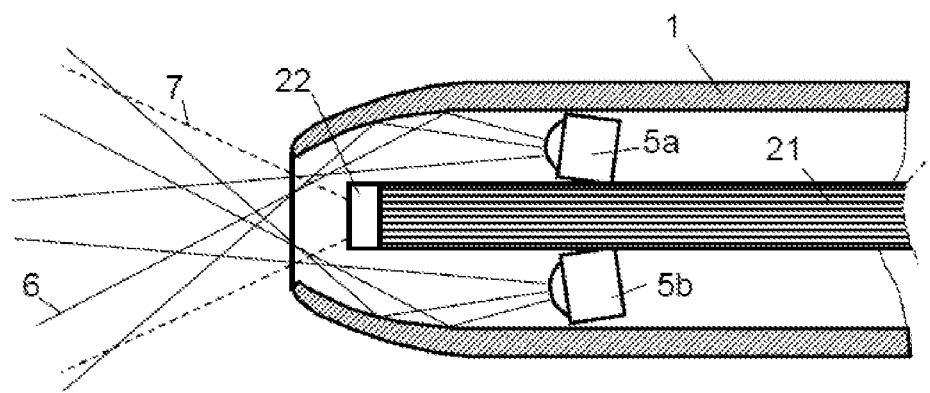
FIG. 7 shows a lengthwise cross section of the tip of a catheter, schematically illustrating an alternate embodiment of imaging using fiber optics and illumination sources behind the fiber optics tip.

FIG. 7 shows a variation on the imaging from FIG. 1a, here using a coherent fiber optics bundle 21 with an imaging lens 22 replacing the camera in FIG. 1a. Here, the camera is arranged to view the free end of the imaging fiber optics outside the patient. The fluid flow around the imaging fiber optics has the same characteristics as in FIG. 1a to share the annular channel for illumination and/or other purposes, and also helps to keep the fiber optics lens clean.

Figure 8:
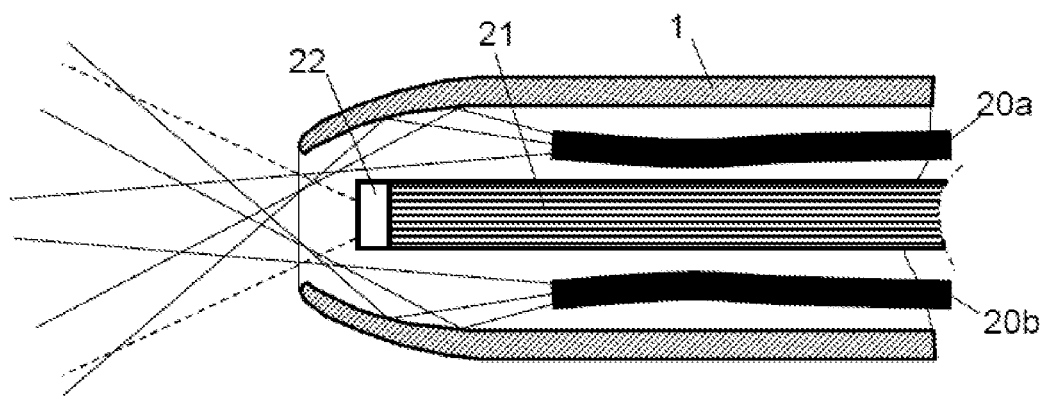
FIG. 8 shows a lengthwise cross section of the tip of a catheter, schematically illustrating an alternate embodiment of both illumination using fiber optics and imaging using fiber optics.

FIG. 8 shows a combination of FIG. 5 and FIG. 6a to utilize remote imaging as well as remote sources. Here, there is an imaging fiber assembly 21 as well as one or more illuminating or treatment fiber optics guides 20a, 20b.

Figure 9:
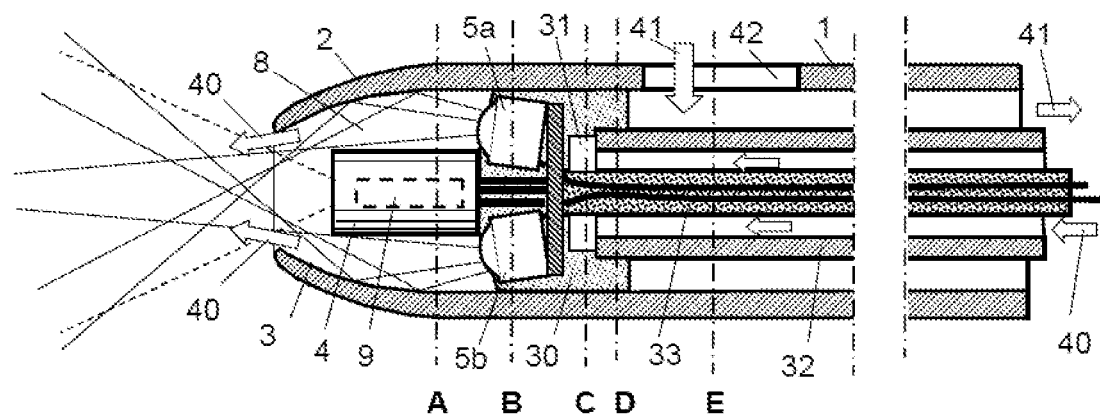
FIG. 9 shows a lengthwise cross section of a catheter with fluid channels, illustrating the principle of a complete assembly.

FIG. 9 shows one embodiment of the device that was schematically illustrated in FIG. 1a, but now expanded with additional details. Fluid flow to the patient 40 enters the inner tubing 32, passes through the distribution channel 31 in the mounting block 30 and emerges from the annular channel 8 in the tip 2. Illumination or treatment sources 5a, 5b send light around the camera 4 though the same annular channel 8 via reflective surfaces 3. Camera 4 may be centered in the tip by supports 9. Fluid flow 41 from the patient enters the aperture 42 in the sleeve 1 and exits via the annular passage between inside of sleeve 1 and outside of inner tube 32. It is noted that for extra high flow rate from the patient, the flow 40 may be reversed and used together with flow 41 to drain the patient faster. The camera 4 (or other sensor) and illumination (or other radiant energy providing) devices 5a, 5b are mounted to a sealed mounting block 30 that holds these devices in place and encapsulates electric connections to the insulated cable 33 that may be fed through the inner tubing 32. In FIG. 9 are also annotated several locations A-E for perpendicular cross sections that are shown in next figure.

Figure 10:
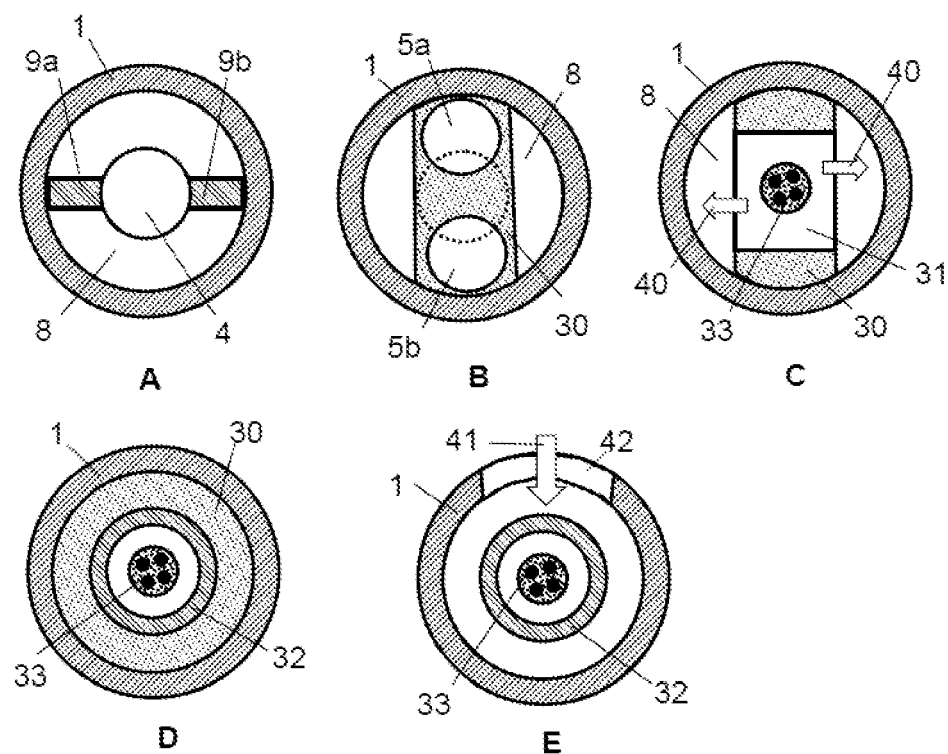
FIG. 10 shows a series of perpendicular cross sections of an embodiment of a catheter with fluid channels, with reference to marked letters A-E in FIG. 9.

FIG. 10 shows a series of perpendicular cross sections from the embodiment of FIG. 9.

Section A shows the camera 4 centered in the annular channel 8 by supports 9a, 9b mounted to the camera.

Section B shows sources 5a, 5b in the mounting block 30 and the apertures for liquid flow in the annular channel 8.

Section C shows the arrangement of flow channel 31 in the mounting block 30 to conduct liquid flow towards the tip.

Section D shows the proximal end of the mounting block 30, here creating a seal between the tip section of the catheter and the long section. This creates two separate fluid sections. The inner tube 32 is attached to the mounting block 30 and provides liquid flow to the tip and also houses and protects insulated electric cable 33.

Section E shows a cross section in line with the aperture 42 in the sleeve 1. Flow 41 from the patient enters the aperture 42 and is led away from the patient in annular passage between sleeve 1 and inner tube 32.

Figure 11:
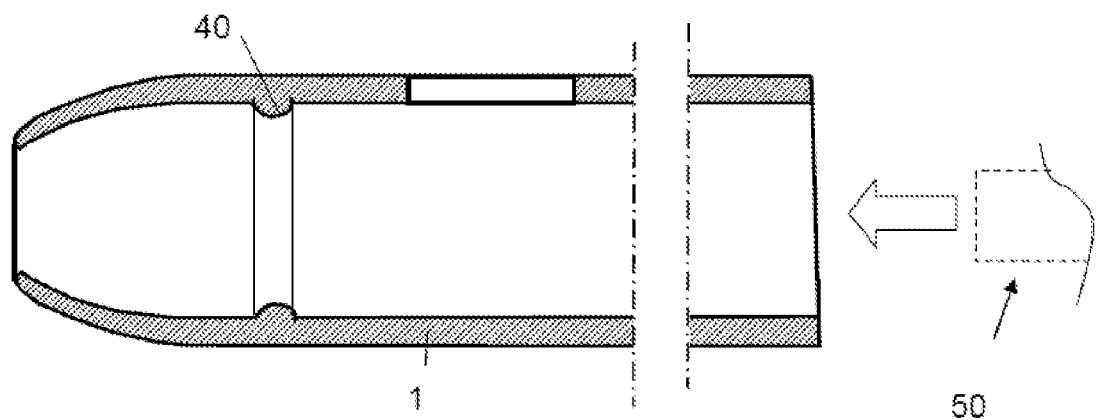
FIG. 11 shows a lengthwise cross section of the sleeve and how the internal assembly can be moved in to the sleeve.
Figure 12:
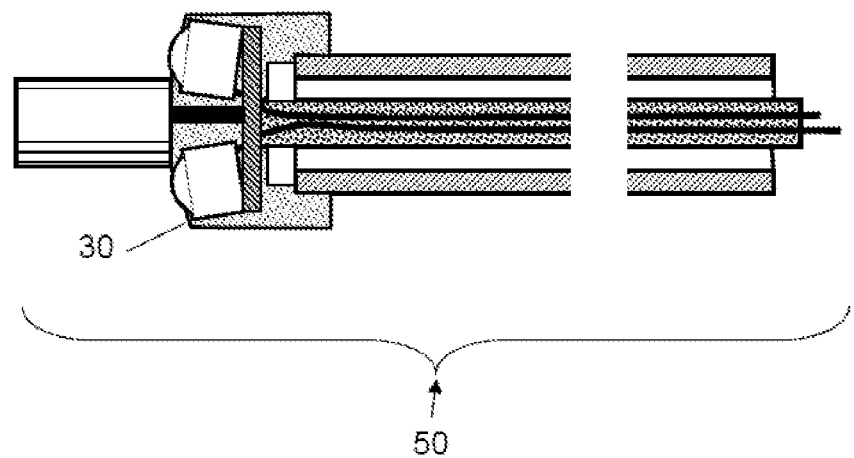
FIG. 12 shows a lengthwise cross section of the internal assembly.

Now going to FIGS. 11 and 12, these show the embodiment of FIG. 9 by its main subassemblies, sleeve 1 including a tapered internally reflective tip, and the inner assembly 50 that consists of all other parts. The inner assembly 50 is inserted from the proximal end of the sleeve 1 and may also use a stop 40 in the sleeve 1 to position it at a desired point. Optionally, the inner assembly 50 may also be positioned anywhere lengthwise inside the sleeve 1 without the stop 40, and positioning may be guided by a vision system image inside the sleeve by internal markings, or all the way to partially extending from the tip as far as it can go.

By this arrangement using a simple and low cost outer sleeve 1 plus an inner assembly with more features, the invention provides flexibility to have different functionality internally using the same insertion sleeve. It also provides as options a completely disposable instrument with a low cost camera, or for re-use and sterilization of the inner assembly with costlier equipment. The inner assembly may thus range from a simple inner tubing to provide desired stiffness or liquid handling of a catheter, to full electro-optics instrumented versions for guiding insertion, diagnosis and treatment.

The other advantage with the arrangement of FIGS. 11 and 12 is the ease of removal of the inner assembly from a patient in i.e., urology extended time catherization. This leaves only the sleeve 9 in place after the visual, diagnostic or treatment insertion procedure is complete. The sleeve 1 may be light weight and have a soft and thin wall design for greater patient comfort and increased inside cross section and can also include local stiffening by selected materials to prevent folding collapse. Additional features known from prior art like retaining balloons on catheters and manifolds at the distal end may be incorporated without deviating from the spirit of the invention.

Figure 13:
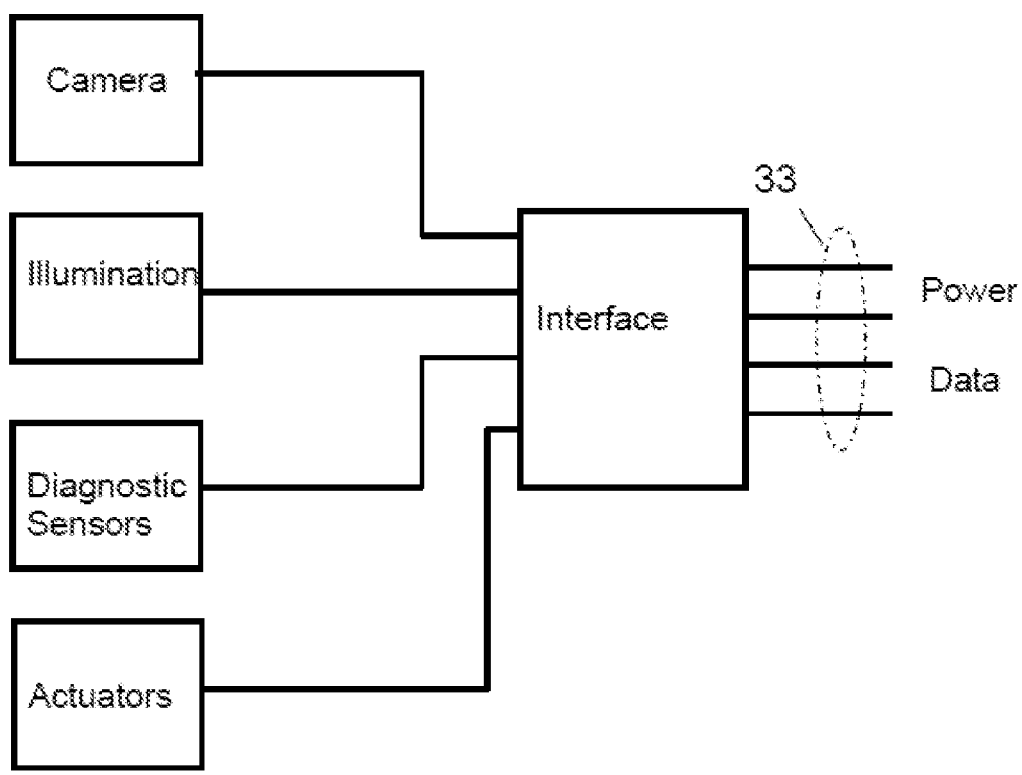
FIG. 13 shows an optional electric diagram for the catheter, for the case where several additional electric devices must be included in the internal assembly.
Figure 1A:
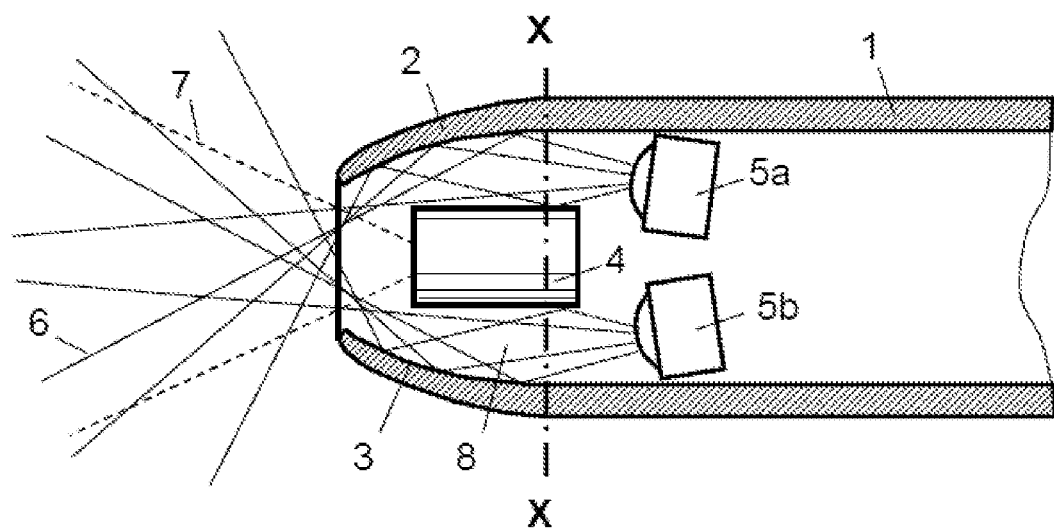
Figure 1B:
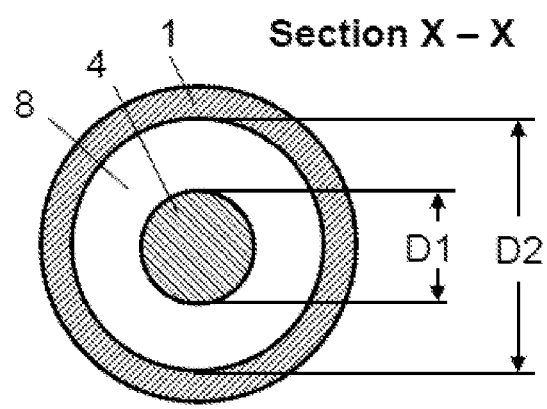
Figure 1C:
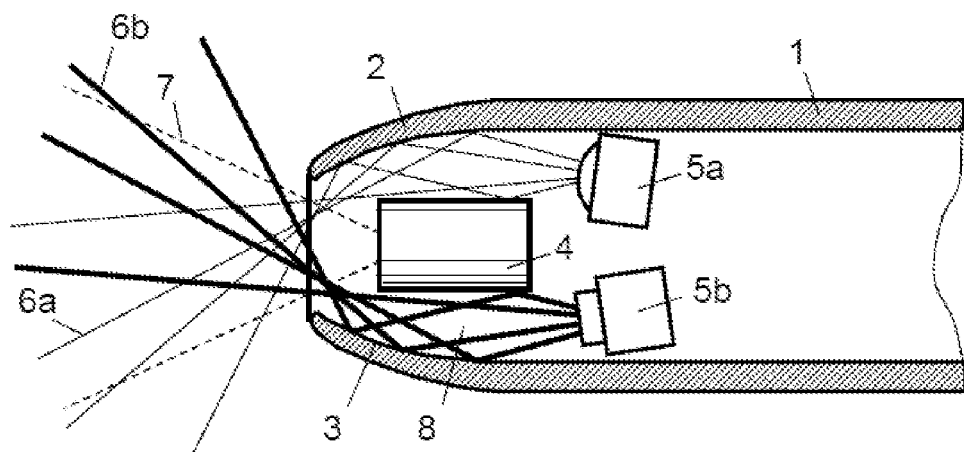
Figure 1D:
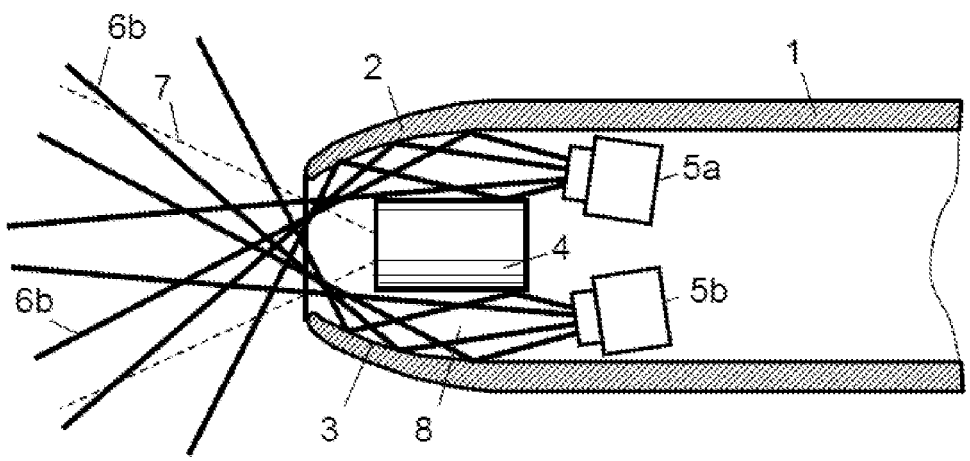
Figure 2A:
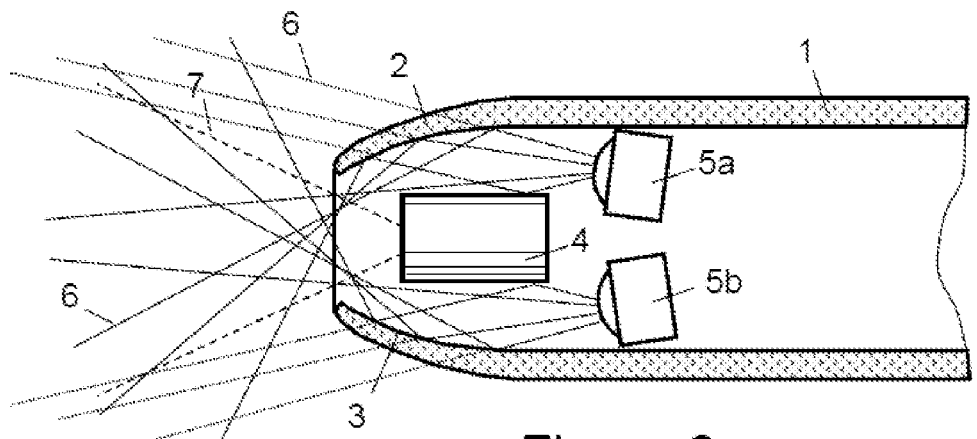
Figure 2B:
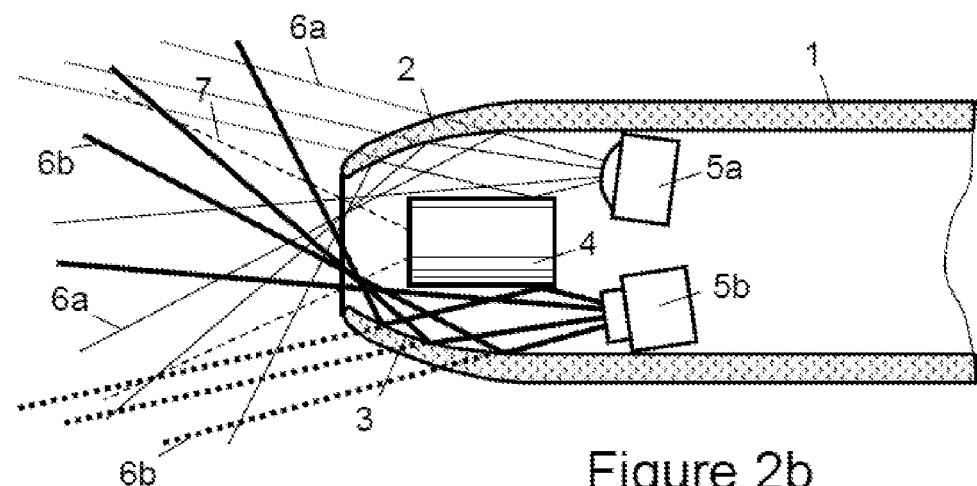
Figure 2C:
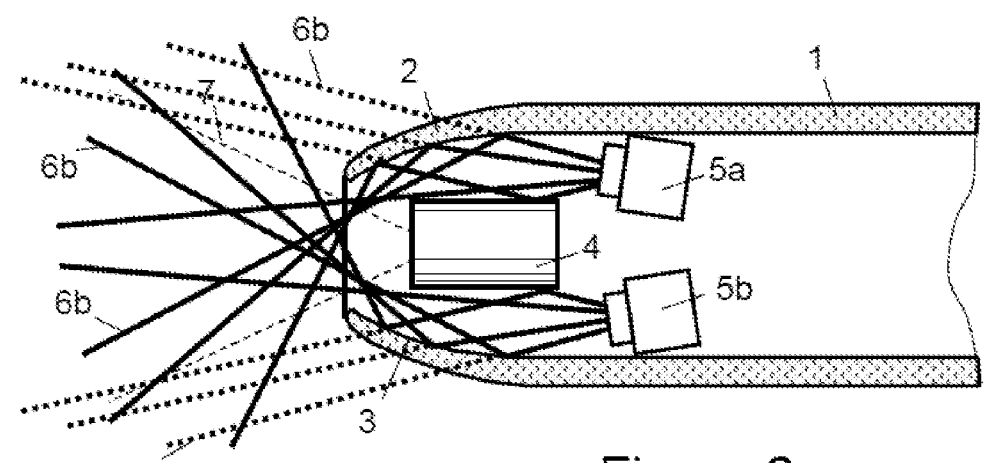
Figure 3:
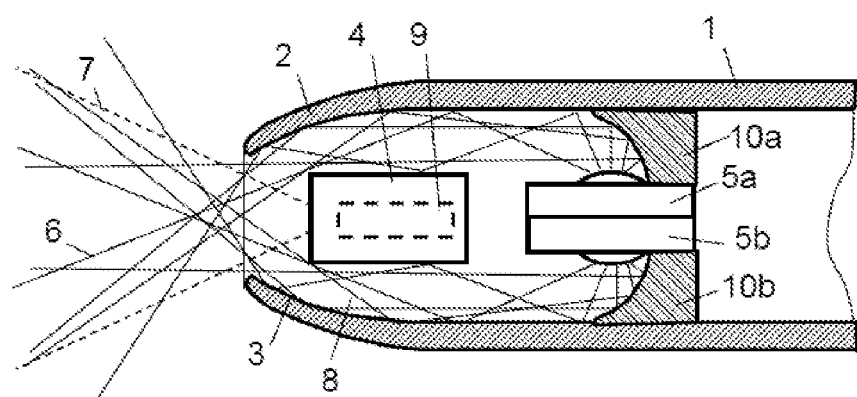
Figure 4:
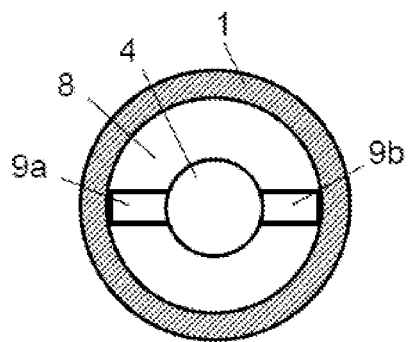
Figure 5:
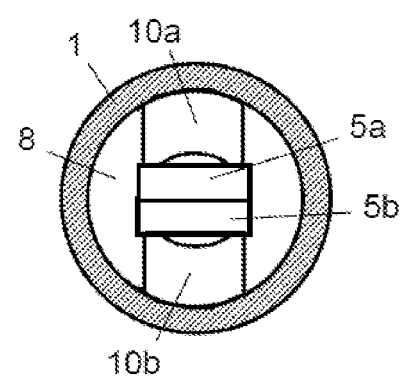
Figure 6A:
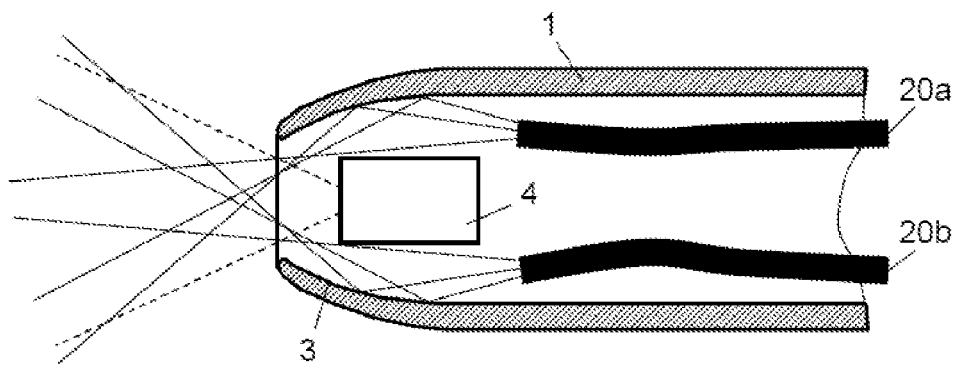
Figure 6B:
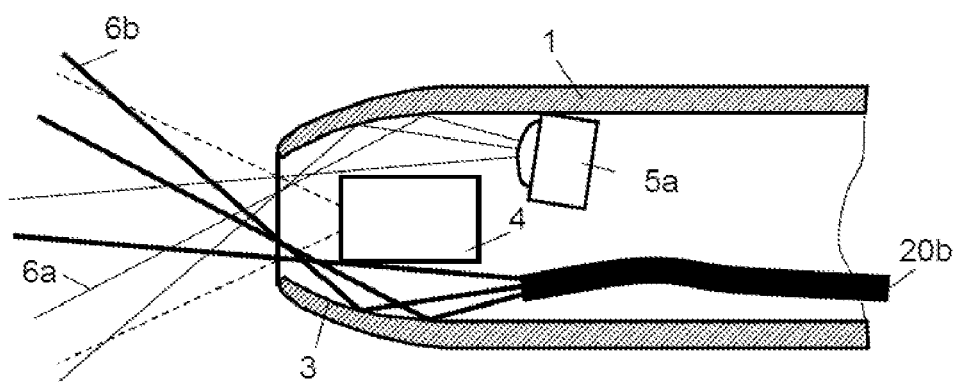
Figure 7:
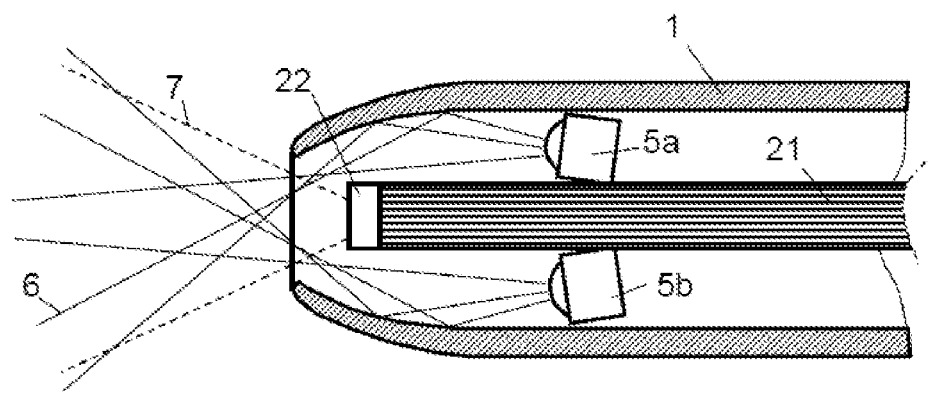
Figure 8:
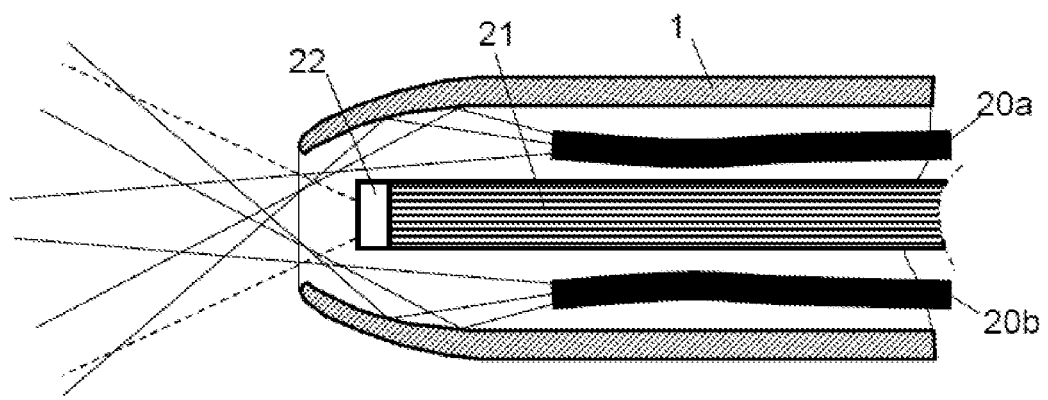
Figure 9:
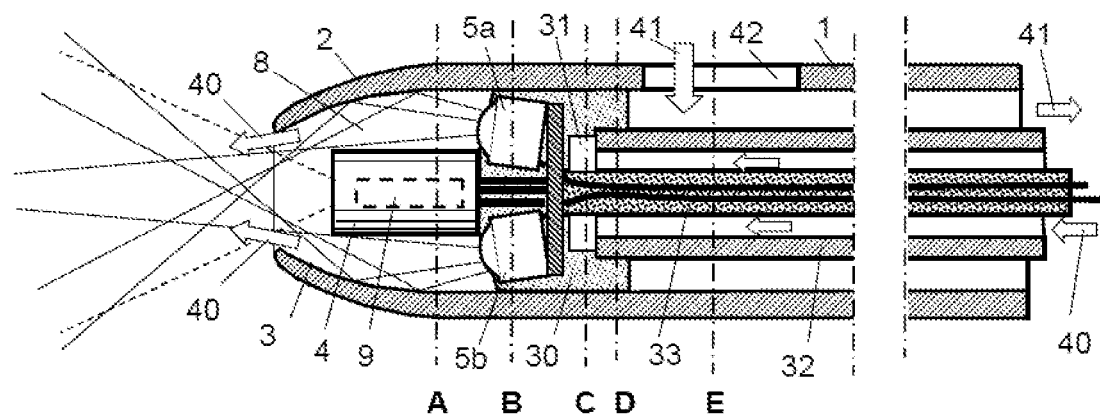
Figure 10:
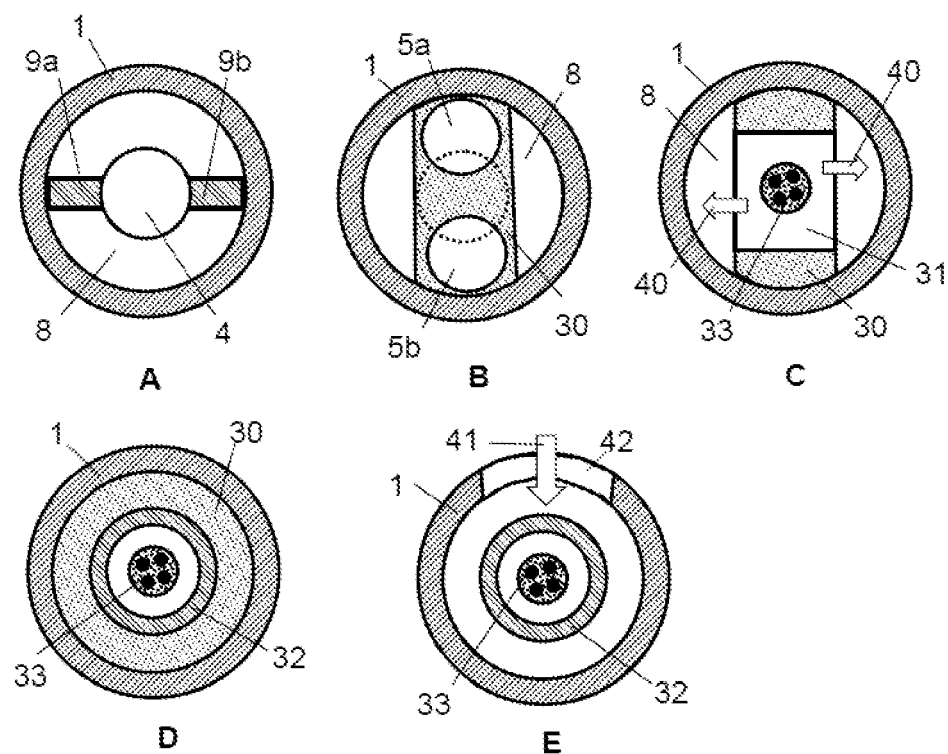
Figure 11:
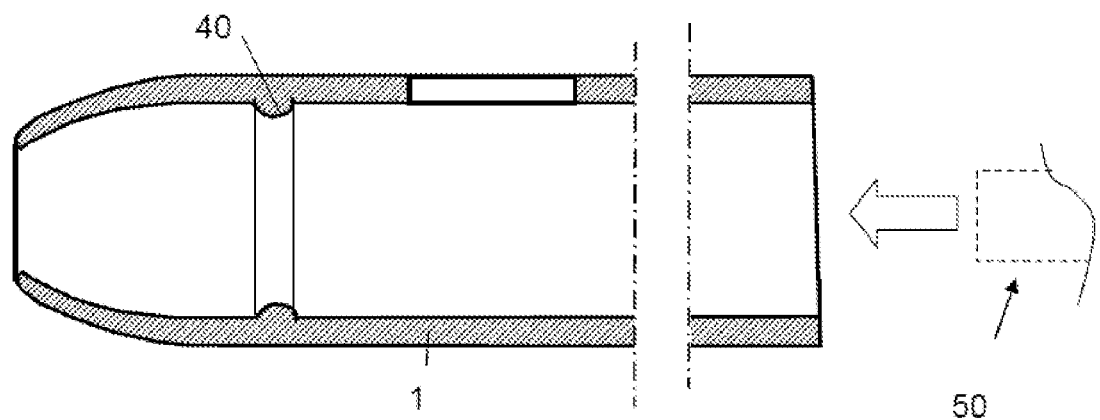
Figure 12:
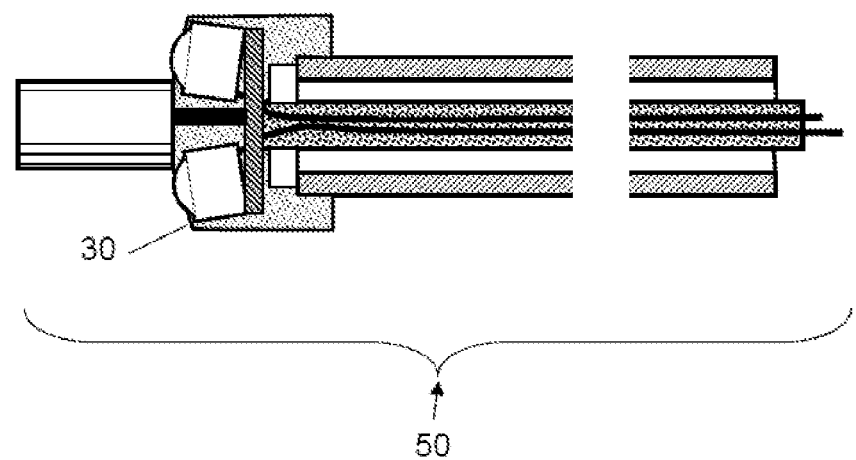
Figure 13:
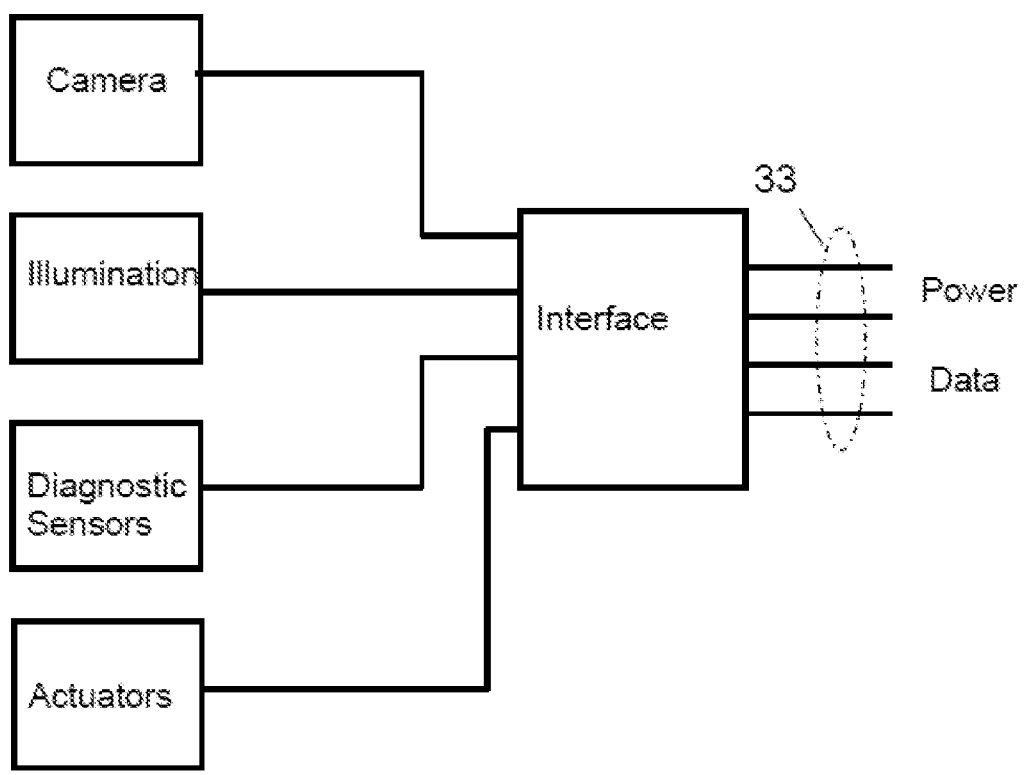

FIG. 13 shows how the invention can accommodate additional functions in the catheter without adding electric wires that interfere with the needed reliability and for minimum cross sectional area for the cable 33. An interface may be provided in the catheter tip that creates a bus structure for connecting additional devices like diagnostic sensors, actuators, and energy control for treatment.

As illustrated in the previous discussion of the embodiments of the invention depicted in the Drawing, the sensed radiant energy and the provided radiant energy are, preferably, both electromagnetic radiation, such as visible light, UV light, IR light, microwave energy, radio frequency energy, terahertz energy or X-ray energy. The radiant energy providing means can provide more than one type of radiant energy, for example, two types of radiant energy. One type of radiant energy can be provided for observation of the internal tissue, while a second type of radiant energy can be provided, for example, for treatment, diagnosis or healing. Where desirable, and practical, illumination need not be used, but one or more other radiant energy sources are provided to focus the same or a mixture of radiant energies onto an internal tissue site.

The catheter internal assembly can be retracted and another internal assembly containing different radiant energy source(s) can be substituted therefor. Even so, preferably the radiant energy providing means and sensing means cooperate to allow a visual inspection of the body lumen.

The sensing means used in the operation of the present invention is well known by itself, and comprises two main parts, the sensor and a conversion/transmitting device. For example, the sensor can be a lens of a camera or a lens operatively connected to a fiber optic bundle. Due to space limitations at the catheter tip and proximal to the catheter tip within the distal catheter section, the radiation providing means is positioned at least behind and to the side of the sensor, for example, the lens, while preferably and where possible, the radiant energy providing means is positioned behind and to the side of the entire sensing means, for example as shown in FIG. 1a of the Drawing. As shown in FIG. 7 of the Drawing, with an elongated sensing means, the radiant energy providing means is positioned behind and to the side of the sensor, which is the imaging lens 22 in FIG. 7.

For diagnostic purposes, the sensing means can be selected in conjunction with the radiant energy providing means to provide a visual image, a thermal image, surrounding temperature, a spectral analysis, a color analysis, a texture analysis, or a fluorescence analysis.

Although the spirit of the invention has been primarily exemplified with a urinary catheter with vision, illumination and fluid handling, the invention can also be applied to catheters in other medical fields; medical or industrial endoscopes, and for other instruments that need to provide radiant energy and fluid handling capability in a confined cross sectional area. As examples of types of medical endoscopes that can usefully employ the inventive features of the present invention, there may be mentioned nasogastric, gynecological, and pulmonary endoscopes.

This invention herein is described by examples of embodiment. The spirit of the invention also permits any combined features from different embodiments. Variations of the invention will be apparent to the skilled artisan.

What is claimed is:

1. A flexible sensing catheter for insertion into and use within a narrow mammalian body lumen or passage, comprising
    an outer catheter sheath having a distal end for insertion into the body lumen or passage,
    a distal catheter section formed within the catheter sheath and in which the outer sheath terminates in an inwardly tapered distal exit and/or inlet port having a distal tip aperture of reduced internal port diameter,
    a sensing system comprising
        a sensing means housed within said catheter distal section near the distal tapered port and having a sensor that has a distal end at a first location, said sensor for sensing a radiant energy directly from the lumen or passage as the catheter travels through or stops within the lumen or passage,
        radiant energy providing means positioned within said catheter distal section in a second location further proximal than the first location and near to the radiant energy sensor of said sensing means, said second location within a larger cross-sectional area of the distal catheter section than the first location,
        radiant energy transmitting means for transmitting radiant energy, provided by the radiant energy providing means into the body lumen or passage, and
        an annular channel formed between the outer sheath and the sensing means,
    said radiant transmitting means configured to transmit the provided radiant energy through the annular channel, around the sensing means, and directly into the body lumen or passage through and from the tapered distal port, wherein the radiant energy transmitting means comprises at least one of a reflective surface on an inner surface of the catheter sheath, and a reflective surface on an outer surface of the sensing means,
    wherein said annular channel is simultaneously usable for transmitting radiant energy through the annular channel and to the body lumen or passage, and as an annular fluid channel through which a fluid is adapted to flow around the sensing means and through the tapered distal port directly to or from the body lumen or passage.

2. The catheter of claim 1 wherein the sensed radiant energy and the provided radiant energy are both electromagnetic radiation.

3. The catheter of claim 2 wherein the provided electromagnetic radiation illuminates the body lumen or passage in front of the catheter.

4. The catheter of claim 3 wherein the sensing means provides a visual inspection of the illuminated body lumen or passage.

5. The catheter of claim 4 wherein the sensor comprises a camera or a lens operatively connected to a fiber optic bundle.

6. The catheter of claim 1 wherein the radiant energy transmitting means comprises at least one mirror and the radiant energy providing means comprises at least one fiber optic bundle.

7. The catheter of claim 1 wherein the provided radiant energy is at least one of visible light, UV light, IR light, microwave energy, radio frequency energy, THz energy and X-ray energy.

8. The catheter of claim 7 wherein the sensing means provides a visual image, a thermal image, surrounding temperature, a spectral analysis, a color analysis, a texture analysis or a fluorescence analysis of tissue within the body lumen or passage.

9. The catheter of claim 4 wherein the radiant energy providing means comprises at least one LED or laser diode providing visible light.

10. The catheter of claim 7 wherein the radiant energy providing means provides at least two kinds of radiant energy.

11. The catheter of claim 10 wherein a first kind of radiant energy is provided for viewing the interior of the body lumen or passage and a second kind of radiant energy is provided for diagnosing or treating or healing a tissue condition within the body lumen or passage.

12. The catheter of claim 1 wherein the sensing system is located within an insertable and removable assembly, whereby the catheter sheath may be left in the patient during and after removal of the assembly.

13. The catheter of claim 12 wherein the assembly comprises a fluid channel for injecting a fluid into the body lumen or passage, or for removing a fluid from the body lumen or passage.

14. The catheter of claim 13 wherein the annular fluid channel usable for injecting a fluid into the body lumen or passage, or for removing a fluid from the body lumen or passage is formed between part of an outer surface of the assembly and an inner surface of the catheter sheath.

15. The catheter of claim 11 wherein the second kind of radiant energy providing means is a laser or light emitting diode.

16. The catheter of claim 1 wherein the radiant energy transmitting means comprises a translucent or semi-translucent catheter sheath at the distal tip, which sheath transmits one energy portion directly through the sheath into the body lumen or passage and reflects another energy portion to pass through the distal tip aperture into the body lumen or passage.

17. The catheter of claim 15 wherein the second kind of radiant energy providing means is a laser diode.

18. A flexible sensing catheter for insertion into and use within a narrow mammalian body lumen or passage, comprising a flexible, thin outer sleeve having a distal end for insertion into the body lumen or passage and terminating at its distal end in an inwardly tapered first distal exit and/or inlet port having a distal tip aperture of reduced internal port diameter, and an insertable and removable assembly for positioning within said outer sleeve, an annular fluid channel being formed between part of said assembly, when positioned in the sleeve, and said sleeve, said channel functioning as a fluid channel for fluid to flow directly to or from a patient through the tapered distal port, said assembly including a distal section, positionable within the outer sheath, and functioning as a fluid channel and containing in said fluid channel (1) a radiant energy sensing means having a sensor for sensing radiant energy, (2) radiant energy providing means positioned proximal and near the sensor of the sensing means and (3) radiant energy transmitting means for transmitting radiant energy provided by said radiant energy providing means through the fluid channel of the assembly, around the sensing means and directly into the body lumen or passage through and the tapered distal port, wherein the radiant energy transmitting means comprises at least one of a reflective surface on an inner surface of the catheter sheath, and a reflective surface on an outer surface of the sensing means and wherein said removable assembly is removable from the outer sleeve while the outer sleeve is in place in the patient.

19. The catheter of claim 18 wherein the radiant energy providing means provides two kinds of radiant energy.

20. The catheter of claim 18 wherein the radiant energy transmitting means comprises a reflective surface on an inner surface of the outer sleeve part located between the radiant energy providing means and the tapered distal port of the catheter, whereby radiant energy is transmitted through the tapered distal port into the body lumen or passage.

21. The catheter of claim 18 wherein the radiant energy providing means is located proximal and near to the sensing means.

22. The catheter of claim 18 containing an electrical interface in the proximal end thereof and configured to provide a reduced wire count bus structure for electric connections.

23. The catheter of claim 18, adapted for providing sensing, radiant energy and fluid handling in a medical field selected from the group consisting of urology, naso-gastronomy, gynecology, and pulmonary endoscopy.

24. The catheter of claim 18 wherein the sensed radiant energy and the provided radiant energy are both electromagnetic radiation.

25. The catheter of claim 24 wherein the provided electromagnetic radiation illuminates the body lumen or passage in front of the catheter.

26. The catheter of claim 25 wherein the sensing means provides a visual inspection of the illuminated body lumen or passage.

27. The catheter of claim 26 wherein the sensor comprises a camera or a lens operatively connected to a fiber optic bundle.

28. The catheter of claim 18 wherein the radiantenergy transmitting means comprises at least one mirror and the radiant energy providing means comprises at least one fiber optic bundle.

29. The catheter of claim 18 wherein the provided radiant energy is at least one of visible light, UV light, IR light, microwave energy, radio frequency energy, THz energy and X-ray energy.

30. The catheter of claim 29 wherein the sensing means provides a visual image, a thermal image, surrounding temperature, a spectral analysis, a color analysis, a texture analysis or a fluorescence analysis of tissue within the body lumen or passage.

31. The catheter of claim 26, wherein the radiant energy providing means comprises at least one LED or laser diode providing visible light.

32. The catheter of claim 29 wherein the radiant energy providing means provides at least two kinds of radiant energy.

33. The catheter of claim 29 wherein a first kind of radiant energy is provided for viewing the interior of the body lumen or passage and a second kind of radiant energy is provided for diagnosing or treating or healing a tissue condition within the body lumen or passage.

34. The catheter of claim 18 wherein the catheter sheath can be left in the patient during removal of the assembly and then a second different sensing system can be inserted into the catheter sheath while the catheter sheath is in place in the patient.

35. The catheter of claim 34 wherein the assembly fluid channel is usable for injecting a fluid into the body lumen or passage, or for removing a fluid from the body lumen or passage.

36. The catheter of claim 18 wherein the annular fluid channel is usable for injecting a fluid into the body lumen or passage, or for removing a fluid from the body lumen or passage.

37. The catheter of claim 33 wherein the second kind of radiant energy providing means is a laser or light emitting diode.

38. The catheter of claim 18 wherein the radiant energy transmitting means comprises a translucent or semi-translucent catheter sheath at the distal tip, which sheath transmits one energy portion directly through the sheath into the body lumen or passage and reflects another energy portion to pass through the distal tip aperture into the body lumen or passage.

39. The catheter of claim 37 wherein the second kind of radiant energy providing means is a laser diode.

40. The catheter of claim 1 wherein the sensor comprises a camera or a lens operatively connected to a fiber optic bundle.

41. The catheter of claim 1 wherein the radiant energy transmitting means comprises at least one mirror and the radiant energy providing means comprises at least one fiber optic bundle.

42. The catheter of claim 1 wherein a first kind of radiant energy is provided for viewing the interior of the body lumen or passage and a second kind of radiant energy is provided for diagnosing or treating or healing a tissue condition within the body lumen or passage.

43. The catheter of claim 1 wherein the sensing system is located within an insertable and removable assembly, whereby the catheter sheath can be left in the patient during removal and a second different sensing system can be inserted into the catheter sheath while it is in place in the patient.

44. The catheter of claim 43 wherein the assembly comprises a fluid channel usable for injecting a fluid into the body lumen or passage, or for removing a fluid from the body lumen or passage.

45. The catheter of claim 44 wherein an annular fluid channel usable for injecting a fluid into the body lumen or passage, or for removing a fluid from the body lumen or passage is formed between part of an outer surface of the assembly and an inner surface of the catheter sheath.

46. The catheter of claim 42 wherein the second kind of radiant energy providing means is a laser or light emitting diode.

47. The catheter of claim 1 wherein the radiant energy transmitting means comprises a translucent or semi-translucent catheter sheath at the distal tip, which sheath transmits one energy portion directly through the sheath into the body lumen or passage and reflects another energy portion to pass through the distal tip aperture into the body lumen or passage.

48. The catheter of claim 46 wherein the second kind of radiant energy providing means is a laser diode.

49. The catheter of claim 1, adapted for providing sensing, radiant energy and fluid handling in a medical field selected from the group consisting of urology, naso-gastronomy, gynecology, and pulmonary endoscopy.

50. The catheter of claim 18 containing an electrical interface in the proximal end thereof and configured to provide a reduced wire count bus structure for electric connections.

* * * * *